United States Patent
Naito et al.

(10) Patent No.: US 7,588,747 B2
(45) Date of Patent: Sep. 15, 2009

(54) SINGLET OXYGEN QUENCHER AND COMPOSITION USING THE SAME

(75) Inventors: Noboru Naito, Saitama (JP); Kumi Kameyama, Tokyo (JP); Akemi Takayama, Saitama (JP); Misako Kobayashi, Tokyo (JP); Yusei Miyamoto, Tokyo (JP); Masashi Kajita, Tokushima (JP)

(73) Assignees: KOSE Corporation, Tokyo (JP); APT Co., Ltd., Tokyo (JP)

( * ) Notice: Subject to any disclaimer, the term of this patent is extended or adjusted under 35 U.S.C. 154(b) by 0 days.

(21) Appl. No.: 10/568,875

(22) PCT Filed: Aug. 20, 2004

(86) PCT No.: PCT/JP2004/012315
§ 371 (c)(1), (2), (4) Date: Sep. 5, 2006

(87) PCT Pub. No.: WO2005/018598
PCT Pub. Date: Mar. 3, 2005

(65) Prior Publication Data
US 2007/0090153 A1 Apr. 26, 2007

(30) Foreign Application Priority Data
Aug. 22, 2003 (JP) .............................. 2003-298188

(51) Int. Cl.
*D01F 9/12* (2006.01)
(52) U.S. Cl. .................................. 423/447.1
(58) Field of Classification Search ........................ None
See application file for complete search history.

(56) References Cited

U.S. PATENT DOCUMENTS

| 5,688,439 | A | 11/1997 | Chopin et al. |
| 2005/0170011 | A1* | 8/2005 | Yanagihara et al. ......... 424/600 |
| 2006/0204593 | A1 | 9/2006 | Miyamoto et al. |

FOREIGN PATENT DOCUMENTS

| EP | 0681992 | | 11/1995 |
| JP | 63-96112 | | 4/1988 |
| JP | 11-60495 | | 3/1999 |
| JP | 2000-232865 | | 8/2000 |
| JP | 2001010954 | * | 1/2001 |
| JP | 2001-122723 | | 5/2001 |
| JP | 2001122723 | * | 5/2001 |
| JP | 2002-241288 | | 8/2002 |
| JP | 2003-81768 | | 3/2003 |
| WO | 99/42112 | | 8/1999 |
| WO | 2004/073722 | | 2/2004 |

OTHER PUBLICATIONS

English Language Abstract of JP 2001-122723.
English Language Abstract of JP 2002-241288.
English Language Abstract of JP 2003-81768.
English Language Abstract of JP 2000-232865.
U.S. Appl. No. 10/545,750 to Yusei Miyamoto et al., filed May 1, 2006 and entitled "Superoxide Anion Decomposition Agent."

* cited by examiner

*Primary Examiner*—Melvin C Mayes
*Assistant Examiner*—Sheng Han
(74) *Attorney, Agent, or Firm*—Greenblum & Bernstein, P.L.C.

(57) ABSTRACT

A novel singlet oxygen quencher is disclosed. The quencher consists of a colloidal liquid of a platinum metal group. A composition comprising, as an active ingredient, the singlet oxygen quencher is also disclosed.

6 Claims, No Drawings

US 7,588,747 B2

SINGLET OXYGEN QUENCHER AND COMPOSITION USING THE SAME

FIELD OF THE INVENTION

The present invention relates to a novel singlet oxygen quencher, and a composition comprising it as an active ingredient.

BACKGROUND ART

Super oxide, hydroxyl radical, hydrogen peroxide and singlet oxygen, and reaction products thereof with metals or lipids have been known as active oxygen species in a broad sense. The active oxygen species, however, typically include reductive molecular species having a different number of electrons from that of ground state oxygen, such as super oxide, hydrogen peroxide and hydroxyl radical, and also include singlet oxygen which is an excited molecular species although having the same number of electrons with that of ground state oxygen, and they individually have specific characteristics, which cannot be understood in terms of the active oxygen species, based on difference in their electron states. Electron spin resonance (ESR) is widely used for detecting the active oxygen species (Example 9 of Japanese Laid-Open Patent Publication "Tokkai" No. 2001-10954, etc., for example). ESR is effective for detecting radical species such as super oxide, hydroxyl radical and the like, but cannot detect singlet oxygen other than radical species. Singlet oxygen in water has a lifetime of as short as approximately 4 microseconds, so that there is only a limited range of detection methods excellent both in sensitivity and specificity (Japanese Laid-Open Patent Publication "Tokkaihei" No. 7-159325, etc. for example). It is therefore supposed that most of reactions ever reported as involving the active oxygen species in a broad sense, and most of agents ever reported as being effective for trapping the active oxygen species are unexplicit with respect to singlet oxygen, if the detection methods are considered.

In recent years, it has been becoming clear, from researches on the reactivity of the individual active oxygen species, that they show specific reactivity respectively to their target molecules. For example, super oxide and hydroxyl radical readily react with proteins to fragment them. On the other hand, singlet oxygen shows a specific reactivity completely different from that of super oxide and the like, such as forming cross-linkage in proteins to thereby polymerize the proteins (J. Soc. Cosmet. Chem. Japan., Vol.28, No.2, 1994, p.163-171, for example). It has also been made clear that, when healthy skin is exposed to ultraviolet irradiation, singlet oxygens are generated in the skin surface, and causes lipid peroxidation of sebum, which is one of factors for various skin troubles (J. Jpn. Cosmet. Sci. Soc., vol.19, No. 1, 1995, p.1-6, for example). Under such circumferences, contribution of singlet oxygen has been regarded as significant even for diseases and ageing which have conventionally been believed as a result of contribution of active oxygen species. Any agent capable of quenching singlet oxygen may therefore be effective for preventing these diseases and ageing. Most of those conventionally known as the singlet oxygen quenchers, however, tend to degrade during storage due to poor chemical stability of the substances per se, and to lower the ability of quenching singlet oxygen, so that they are in need of further improvement in terms of sustainability of the effect.

DISCLOSURE OF THE INVENTION

Problems to be Solved by the Invention

An object of the present invention is to provide an agent capable of keeping a desirable ability of quenching singlet oxygen for a long period. Another object of the present invention is to provide a singlet oxygen quencher and a composition, capable of depressing various reactions caused by singlet oxygen. Still another object of the present invention is to provide a singlet oxygen quencher and a composition, capable of preventing ageing of skin, pigmentation of skin and damage of skin, partially ascribable to reactions involving singlet oxygen, when applied to the skin.

In order to solve the above problems, the present invention provides a singlet oxygen quencher consisting of a colloidal liquid or a platinum group metal.

As an embodiment of the present invention, there is provided the singlet oxygen quencher having a rate constant for quenching singlet oxygen of $1.0 \times 10^8$ $M^{-1}$ $s^{-1}$ or above; the singlet oxygen quencher wherein the platinum group metal is platinum or rhodium; the singlet oxygen quencher consisting of a colloidal liquid of a single metal species; the singlet oxygen quencher consisting of a platinum colloidal liquid or a rhodium colloidal liquid; the singlet oxygen quencher wherein the colloidal liquid comprises colloid particles of a platinum group metal prepared by a metal salt reduction process; the singlet oxygen quencher comprising colloid particles having a particle size of 1 to 6 nm or around; the singlet oxygen quencher wherein the colloidal liquid further comprises a water-soluble polymer; the singlet oxygen quencher wherein a mass ration of the platinum group metal to the water-soluble polymer is from 1/40 to 1/100; or the singlet oxygen quencher wherein the water-soluble polymer is poly (1-vinyl-2-pyrrolidone). The singlet oxygen quencher of the present invention or a composition comprising it as an active ingredient is useful in depressing various reactions in which singlet oxygen is involved, and can be used as a collagen cross-linkage inhibitor, immediate pigment darkening inhibitor, enzyme inactivation inhibitor, lipid peroxidation inhibitor, cellular ageing inhibitor or color fading inhibitor.

In another aspect, the present invention provides a composition comprising, as an active ingredient, the singlet oxygen quencher; an external preparation for skin comprising, as an active ingredient, the singlet oxygen quencher; a method for depressing collagen cross-linkage, immediate pigment darkening, enzyme inactivation, lipid peroxidation or cellular ageing, comprising applying the singlet oxygen quencher or the composition comprising it as an active ingredient to the skin; a method for preventing the skin from aging, comprising applying the singlet oxygen quencher or the composition comprising it as an active ingredient to the skin; and a process for preparing an external preparation for skin, comprising adding a colloidal liquid of a platinum group metal.

Effect of the Invention

According to the present invention, there is provided a singlet oxygen quencher capable of keeping a desirable ability of quenching singlet oxygen for a long period. According to the present invention, there is also provided a singlet oxygen quencher and a composition, capable of depressing various reactions caused by singlet oxygen. According to the present invention, there is also provided a singlet oxygen quencher and a composition, capable of preventing ageing of skin, pigmentation of skin and damage of skin, ascribable to reactions in which singlet oxygen is involved, when applied to the skin.

BEST MODES FOR CARRYING OUT THE INVENTION

The singlet oxygen quencher of the present invention comprises a colloidal liquid of a platinum group metal. The platinum group metal generally refers to transition metals consisting of ruthenium, osmium, rhodium, iridium, palladium and platinum. Among others, rhodium and platinum are preferable. The colloidal liquid refers to a dispersion of particles of these platinum group metals in a liquid phase. The colloidal liquid may be such as containing any one element selected from the platinum group metals, or may be such as containing two or more metal species. Among others, a colloidal liquid of a single metal species is preferable, and platinum colloidal liquid or rhodium colloidal liquid is preferable.

The colloidal liquid of a platinum group metal refers to a dispersion of particles of a platinum group metal in a liquid phase. In view of obtaining a stable colloidal state, the particles of a platinum group metal preferably have a relatively large specific surface area and have an excellent surface reactivity. There is no special limitation on the particle size of the platinum group metal, and it is preferably 50 nm or smaller, more preferably 20 nm or smaller, still more preferably 10 nm or smaller, and particularly preferably 1 to 6 nm or around. Mean particle size of the colloidal particles can be determined by observation under a transmission electron microscope.

A major ingredient of the liquid phase into which the platinum group metal is dispersed is preferably water. It is also allowable to add an organic solvent, so far as the colloidal state is not destabilized. Examples of the organic solvents include alcohols such as methanol, ethanol, etc., and polyhydric alcohols such as glycerin, diglycerin, 1,3-butylene glycol, dipropylene glycol, etc.

There are various known methods of producing metal particles (for example, Japanese Examined Patent Publication "Tokkosho" No. 57-43125, ditto No. 59-120249, Japanese Laid-Open Patent Publication "Tokkaihei" No. 9-225317, ditto No. 10-176207, Japanese Laid-Open Patent Publication "Tokkai" No. 2001-79382 and ditto No. 2001-122723), and those skilled in the art can readily prepare the metal particles referring to these methods. For example, as a method of producing the metal particles, available methods include chemical process known as precipitation process or metal salt reduction process; or physical process known as combustion process. Any particles prepared by any process may be used in for preparation of the singlet oxygen quencher of the present invention, wherein it is preferable to use the metal particles prepared by the metal salt reduction process, in view of simplicity of the production and from aspect of quality.

In the metal salt reduction process, the metal particles can be obtained typically by preparing an aqueous solution or an organic solvent solution of a water-soluble or an organic-solvent-soluble metal salt or metal complex, adding a water-soluble polymer to the solution, adjusting the pH if necessary, and refluxing the mixture under heating in an inert atmosphere to thereby reduce the metal salt. Examples of the water-soluble or organic-solvent-soluble metal salt include, however there is no special limitation thereof, acetate, chloride, sulfate, nitrate, sulfonate, phosphate or the like, or complexes of them.

Examples of the water-soluble polymer, which can be used for the metal salt reduction process, include, however there is no specific limitation of thereof, polyvinyl pyrrolidone, polyvinyl alcohol, polyacrylic acid, cyclodextrin, aminopectin, methyl cellulose or the like, or combination of two or more species of them. It is preferable to use polyvinyl pyrrolidone, and more preferable to use poly(1-vinyl-2-pyrrolidone). Ratio of concentration of the platinum group metal to the water-soluble polymer, preferably poly(1-vinyl-2-pyrrolidone), based on the unit formula weight preferably falls in the range from 1/40 to 1/200. It is also possible to use, in place of, or in combination with the water-soluble polymer, a variety of surfactants such as anionic, cationic, amphoteric, nonionic, or lipid-soluble surfactants. For the case where alcohol is used for the reduction, it is general to use ethanol, n-propanol, n-butanol, n-amyl alcohol or ethylene glycol, and the like. After generation of the metal particles in the liquid phase, these water-soluble polymer and surfactants contribute to stabilization of the colloidal state as a protective colloid. Methods of preparing the metal particles are, of course, not limited to those explained in the above.

It is also allowable to use the metal particles, produced in the liquid phase by the metal salt reduction process, directly for preparation of the singlet oxygen quencher without being separated from the liquid phase. For example, the singlet oxygen quencher of a stable colloidal liquid can be prepared by producing metal particles in the liquid phase by the metal salt reduction process, carrying out an appropriate purification if necessary (for example, removal of an organic solvent used in the metal salt reduction process under reduced pressure), and adding an arbitrary amount of water, of by removing an arbitrary amount of water. It is also allowable to optionally add a surfactant, dispersant and the like which contributes to stabilization of the colloidal state. The method of preparing the singlet oxygen quencher of the present invention is, of course, not limited to the above, and, for example, the metal particles produced by the metal salt reduction process may be once separated from the liquid phase and re-dispersed into a liquid phase mainly composed of water.

Concentration of the platinum group metal in the colloidal liquid as a mother liquor used for the final product is not specifically limited, and is allowed in a range not causative of destabilization of the colloidal state. The stability can generally be maintained within the range from 1 nmol/L to 1 mmol/L or around, but the range is not limited thereto, because the stability of the colloidal state varies depending on the respective metals. Preferable ranges of concentration of the platinum group metal in the composition as the final product will be described later.

The singlet oxygen quencher of the present invention preferably has a rate constant for quenching singlet oxygen of $1.0 \times 10^8$ $M^{-1}s^{-1}$ or above, more preferably $1.0 \times 10^9$ $M^{-1}s^{-1}$ or above, and still more preferably $1.0 \times 10^{10}$ $M^{-1}s^{-1}$ or above. In this description, "rate constant for quenching singlet oxygen" refers to a reaction rate constant (kq) appears in the Stern-Volmer equation ($I_0/I = 1 + kq \cdot \tau \cdot Cq$). More specifically, the constant can be calculated based on the Stern-Volmer equations by adding various concentrations (Cq) of the singlet oxygen quencher to a system in which singlet oxygen is intentionally produced and thereby light emission-ascribable to transition of singlet oxygen can be observed, measuring the emission intensity (I), calculating ratios ($I_0$)/(I) with respect to emission intensity ($I_0$) observed without addition of the quencher, and by plotting the ratios for the individual concentration values (Cq). In the above equation, σ represents a lifetime of singlet oxygen, and is a constant variable depending on solvent of the system. Concentration Cq represents a metal concentration, expressed in mol/L. As for an experiment system used for calculating the rate constant for quenching singlet oxygen, and a detector of the emission, those described in Japanese Patent Publication No. 3356517 are adoptable.

The singlet oxygen quencher of the present invention is not oxidized during working and does not lose the effect, so that it can have the ability of quenching singlet oxygen for a long period.

The singlet oxygen quencher of the present invention is adoptable to any applications for depressing reactions induced or accelerated by the presence of singlet oxygen. For example, singlet oxygen is known to crosslink collagen, which is a dermis constituent (J. Soc. Cosmet. Chem. Japan., Vol.28, No.2 1994, p.163-171). Cross-linkage of collagen lowers elasticity and softness of the skin, and is a factor of skin ageing. Employing the singlet oxygen quencher of the present invention makes it possible to inhibit formation of cross-linkage of collagen, to prevent the skin from ageing, and to keep the skin youthfully. That is, the singlet oxygen quencher of the present invention can be used as a collagen cross-linkage inhibitor.

Singlet oxygen is also known to be generated in a large amount in the skin surface irradiated by UV-A, to be involved in immediate pigment darkening caused by oxidation of DOPA, and to be involved in lipid peroxidation of sebum (J. Jpn. Cosmet. Sci. Soc., vol.19, No.1, 1995, p.1-6). The singlet oxygen quencher of the present invention can therefore be used, when applied to the skin, as an inhibitor capable of depressing the immediate pigment darkening or the peroxidation of sebum. For the case where the singlet oxygen quencher of the present invention is used as an instantaneous melanism inhibitor, the rate constant for quenching singlet oxygen of the singlet oxygen quencher is more preferably larger than that of DOPA, that is, $6.8 \times 10^8$ $M^{-1}s^{-1}$ or above. Singlet oxygen is also known to cause, for example, inactivation of various enzymes involved in biological reactions. The singlet oxygen quencher of the present invention can therefore be used as an enzyme inactivation inhibitor. For the case where the singlet oxygen quencher of the present invention is used as an enzyme inactivation inhibitor, the rate constant for quenching singlet oxygen of the singlet oxygen quencher is preferably larger than the rate constant for quenching singlet oxygen of the relevant enzyme.

The present inventors also reported that singlet oxygen relates to cellular ageing, using a cell ageing evaluation system for the purpose of studying on in vivo ageing (J. Jpn. Cosmet. Sci. Soc., Vol.26, 2002, p.79-85). In particular, a characteristic ageing phenomenon such as shortened cellular lifespan was observed when cells were exposed to singlet oxygen. The phenomenon was prevented by adding histidine, which is a singlet oxygen quencher. This suggests that the singlet oxygen quencher has effects of inhibiting cell ageing, and of consequently retarding in vivo ageing. The singlet oxygen quencher of the present invention can therefore be used as a cellular ageing inhibitor.

Singlet oxygen is also known to induce or accelerate fading or discoloration of dyes such as plant extracts compounded into cosmetics and foods. Even for the case without fading or discoloration, presence of singlet oxygen may induce or promote decomposition of drug component compounded to skincare cosmetics. Compounding of the singlet oxygen quencher of the present invention is not only successful in obtaining the singlet oxygen quenching ability and associated effects described in the above, but also in obtaining an effect of preventing decomposition of other components compounded therewith. In other words, the singlet oxygen quencher of the present invention is also applicable as a color fading inhibitor, but not limited thereto, allowing use as a preservative for other active ingredients.

A composition containing the singlet oxygen quencher of the present invention is applicable to various purposes including pharmaceutical products, quasi-pharmaceutical products, cosmetics, foods and the like. Because singlet oxygen is abundant in the skin surface, which is always contacted with oxygen and exposed to ultraviolet radiation, so that the composition comprising the singlet oxygen quencher of the present invention is more useful as an external preparation for skin. Reactions possibly prevented by quenching of singlet oxygen are such as those causative of ageing of skin, pigmentation of skin and damage of skin, so that the singlet oxygen quencher and the composition containing it as an active ingredient are particularly useful as skincare cosmetics capable of depressing such reactions, targeted at anti-ageing, whitening and aesthetic of skin.

The external preparation for skin can be prepared by independently using the singlet oxygen quencher of the present invention, or by compounding it with one or more known additives for external pharmaceutical products or with additives for skincare cosmetics according to general methods. The amount of compounding of the singlet oxygen quencher of the present invention in the external preparation may vary depending on formation, intended use and the like, and also on singlet oxygen quenching ability of the singlet oxygen quencher, wherein general concentration of the platinum group metal in the final composition preferably falls in the range from 0.01 nmol/L to 50 µmol/L, and more preferably from 1 nmol/L to 1 µmol/L. Keeping these ranges makes it possible to stably compound the colloidal liquid, and to exhibit an excellent efficiency.

The singlet oxygen quencher of the present invention can independently be used as an external preparation for skin, or can be prepared in a form of an external preparation for skin by being compounded with one or more additives. The additives optionally used include those generally used for skincare cosmetics and external pharmaceutical products, such as water (purified water, spring water, deep sea water, etc.), alcohol, oil solution, surfactant, metal soap, gelling agent, powder, alcohols, water-soluble polymer, film-forming agent, resin, ultraviolet barrier agent, clathrate compound, antibacterial agent, flavoring ingredient, deodorizer, salts, pH adjusting agent, cooling agent, animal and microbial extracts, plant extract, blood circulation promoter, astringent, anti-seborrheic agent, whitener, anti-inflammatory agent, active oxygen scavenger other than the singlet oxygen quencher of the present invention, cell activator, moistener, chelating agent, keratolytic, enzyme, hormones, vitamins and so forth. The external preparation for skin can be prepared according to the general methodologies, and the amount of compounding of the above-described additives can be determined again according to the general methodologies within ranges not causative of impairing the effects of the present invention.

Formation of the external preparation for skin is not specifically limited, wherein allowable forms include those belonging to skincare cosmetics such as moisturizer, cream, skin lotion, beauty essence, pack, cleansing agent, makeup cosmetics and so forth; those belonging to hair-care cosmetics such as shampoo, hair treatment, hair styling agent, hair restoration tonic, hair growth tonic and so forth; and those belonging to external medicines such as dispersion, ointment, aerosol, patch, cataplasm, liniment and so forth.

EXAMPLES

Paragraphs below will more specifically describe the present invention referring to Examples, wherein the scope of the present invention is by no means limited by Examples below.

Example 1

Poly(1-vinyl-2-pyrrolidone) (product of Wako Pure Chemical Industries, Ltd., 0.147 g) was placed in a 100-mL double-necked egg plant flask connected with an Allihn condenser and a three-way cock, and was dissolved with 23 mL of distilled water. The resultant solution was stirred for 10 minutes, added with a $1.66 \times 10^{-2}$ M solution (2 mL) prepared by dissolving platinous chloride ($H_2PtCl_6 \cdot 6H_2O$, product of Wako Pure Chemical Industries, Ltd.) into distilled water, and stirred for additional 30 minutes. After replacing the atmosphere in the reaction system with nitrogen, 25 mL of special-grade ethanol, was added to the reaction system, and the mixture was refluxed at 100° C. for 2 hours under the nitrogen atmosphere. UV spectrum of the reaction liquid was measured to confirm disappearance of a platinum ion peak and saturation of peak ascribable to scattering specific to the solid metal, and the reduction was terminated. The organic solvent was removed under reduced pressure to obtain a platinum colloidal liquid (mean particle size: 2.4±0.7 nm). Platinum concentration of thus obtained platinum colloidal liquid was 1 mmol/L.

Example 2

A rhodium colloidal liquid (mean particle size: 2.2±1.0 nm) was prepared in the same manner as described in Example 1, except that a $1.6 \times 10^{-2}$ M solution of rhodium chloride trihydrate (product of Wako Pure Chemical Industries, Ltd.) was used in the place of the $1.66 \times 10^{-2}$ M platinous chloride solution. Rhodium concentration of thus obtained rhodium colloidal liquid was 1 mmol/L.

Example 3

Rate constants for quenching singlet oxygen of thus prepared platinum colloidal liquid and rhodium colloidal liquid were calculated according to the above-described method using the Stern-Volmer equation ($I_0/I = 1 + kq \cdot \sigma \cdot Cq$). A detector of singlet oxygen was such as described in Japanese Patent Publication No. 3356517 (details are given in paragraph [0026] in this publication). A 200-µM aqueous solution of rose bengal was circulated in a flow cell. When the cell was irradiated by a 514.5-nm laser light, which has an absorption wavelength of rose bengal, light emission in association with transition of singlet oxygen was observed, showing an emission peak of 1268 nm. The solution was then added with various concentrations of the platinum colloidal liquid and the rhodium colloidal liquid (ranging from 1 to 10 µmol/L of platinum and rhodium) respectively, emission intensities (I) were measured, ratios of intensities ($I_0$)/(I) to emission intensity ($I_0$) observed under no addition of the quencher were calculated, and plotted with respect to the individual concentrations (Cq: respective concentrations of platinum and rhodium). Rate constants for quenching singlet oxygen (kq) were calculated from the Stern-Volmer equation described in the above. Results are shown below.

rhodium colloidal liquid: $2.4 \times 10^{10} M^{-1} s^{-1}$ platinum colloidal liquid: $1.6 \times 10^{10} M^{-1} s^{-1}$ Similar calculation of the rate constant for quenching singlet oxygen made on various compounds conventionally known as active oxygen quenchers or singlet oxygen quenchers showed a rate of $7 \times 10^9$ $M^{-1}s^{-1}$ for β-carotene, $7.9 \times 10^8$ $M^{-1}s^{-1}$ for sodium azide, $8.3 \times 10^6$ $M^{-1}s^{-1}$ for ascorbic acid, $1 \times 10^6$ $M^{-1}s^{-1}$ for hypotaurin, and $1 \times 10^4$ $M^{-1}s^{-1}$ for mannitol. These results demonstrated that the rhodium colloidal liquid and the platinum colloidal liquid showed singlet oxygen quenching abilities more excellent than those of the compound conventionally known as active oxygen quenchers or singlet oxygen quencher. The rhodium colloidal liquid and the platinum colloidal liquid may be hardly oxidized themselves during storage, and can keep their singlet oxygen quenching abilities for a long time, without losing the abilities.

Example 4

Skin Lotion

A solution prepared by mixing shown below ingredients (3), (4), and (8) to (10) and dissolving therein, and a solution preparing by mixing shown below ingredients (1), (2), (5) to (7) and (11) and dissolving therein were homogeneously mixed to obtain a skin solution.

| (Ingredients) | (%) |
|---|---|
| (1) glycerin | 5.0 |
| (2) 1,3-butylene glycol | 6.5 |
| (3) polyoxyethylene (20 E.O.) sorbitan monolaurate | 1.2 |
| (4) ethanol | 8.0 |
| (5) platinum colloidal liquid (platinum concentration: 100 nmol/L) | 10.0 |
| (6) lactic acid | 0.05 |
| (7) sodium lactate | 0.1 |
| (8) 2-ethylhexyl para-methoxycinnamate | 3.0 |
| (9) preservative | Optimum amount |
| (10) fragrance | Optimum amount |
| (11) purified water | balance |

Example 5

Moisturizer

Ingredients (8) and (9) shown below were added to ingredient (12), the mixture was allowed to swell, added and mixed with ingredient (10), heated and kept at 70° C., to thereby prepare an aqueous phase. Ingredients (1) to (6) shown below were heated and mixed at 70° C., the mixture was added to the aqueous phase, and allowed to emulsify. The emulsified product was cooled to room temperature, added with ingredients (7), (11) and (13) shown below, and homogeneously mixed to obtain a moisturizer.

| (Ingredients) | (%) |
|---|---|
| (1) polyoxyethylene (10 E.O.) sorbitan monostearate | 1.0 |

-continued

| (Ingredients) | (%) |
|---|---|
| (2) polyoxyethylene (60 E.O.) sorbit tetraoleate | 0.5 |
| (3) glyceryl monostearate | 1.0 |
| (4) stearic acid | 0.5 |
| (5) behenyl alcohol | 0.5 |
| (6) squalane | 8.0 |
| (7) rhodium colloidal liquid (rhodium concentration: 1 μmol/L) | 5.0 |
| (8) preservative | 0.1 |
| (9) carboxyvinyl polymer | 0.1 |
| (10) sodium hydroxide | 0.05 |
| (11) ethanol | 5.0 |
| (12) purified water | balance |
| (13) fragrance | Optimum amount |

Both of the prepared skin lotion and moisturizer were free from any changes in color and odor, and precipitation, and found to be applicable to skin.

INDUSTRIAL APPLICABILITY

The singlet oxygen quencher of the present invention or the composition comprising it as an active ingredient has singlet oxygen quenching ability, and is useful in depressing reactions in which singlet oxygen is involved, in particular various reactions in which the singlet oxygen is involved, which are causatives of ageing of skin, instantaneous melanism, damage of skin and so forth.

The invention claimed is:

1. A singlet oxygen quencher consisting of a colloidal liquid of at least one platinum metal group member and a water soluble polymer, wherein
   the at least one platinum metal group member is chosen from platinum and rhodium;
   the platinum metal group member has a particle size equal to or smaller than 50 nm; and
   the water soluble polymer is chosen from polyvinyl pyrrolidone, polyvinyl alcohol, polyacrylic acid, cyclodextrin, aminopectin, methyl cellulose, and combinations thereof.

2. The singlet oxygen quencher as set forth in claim 1 having a rate constant for quenching singlet oxygen of $1.0 \times 10^8 M^{-1} s^{-1}$ or above.

3. The singlet oxygen quencher as set forth in claim 1, wherein the colloidal liquid is a colloidal liquid of a single platinum metal group member.

4. The singlet oxygen quencher as set forth in claim 1, used as a collagen cross-linkage inhibitor, instantaneous melanism inhibitor, enzyme inactivation inhibitor, lipid hyperoxidation inhibitor, cell ageing inhibitor or color fading inhibitor.

5. A composition comprising as an active ingredient a singlet oxygen quencher as set forth in claim 1.

6. The singlet oxygen quencher as set forth in claim 1, wherein the colloidal liquid of the at least one platinum metal group member is prepared according to a metal salt reduction process.

* * * * *